United States Patent [19]

Griffiths

[11] Patent Number: 4,818,870

[45] Date of Patent: Apr. 4, 1989

[54] AIR WITHDRAWING SAMPLING PROBES FOR A CONTRABAND DETECTION SYSTEM

[75] Inventor: Frank K. Griffiths, Bracknell, Great Britain

[73] Assignee: British Aerospace PLC, London, England

[21] Appl. No.: 46,927

[22] Filed: May 5, 1987

[30] Foreign Application Priority Data

May 6, 1986 [GB] United Kingdom ............... 8611031

[51] Int. Cl.$^4$ .................................... H01J 49/04
[52] U.S. Cl. ........................... 250/288; 250/281; 73/864.81; 73/864.73
[58] Field of Search ............... 250/288, 281; 73/864.21, 864.81, 864.73, 863.85; 285/316, 315, 319

[56] References Cited

U.S. PATENT DOCUMENTS 2,784,987  3/1957  Corcoran ........................... 285/316
4,298,795  11/1981  Takeuchi et al. ................. 250/288 A

FOREIGN PATENT DOCUMENTS 180300  11/1968  United Kingdom ............ 73/864.73
2162944  2/1986  United Kingdom .

Primary Examiner—Bruce C. Anderson
Assistant Examiner—John A. Miller
Attorney, Agent, or Firm—Cushman, Darby & Cushman

[57] ABSTRACT

A sampling probe, particularly suitable for use in withdrawing air from a cargo container and leading the withdrawn air towards a mass analyser to check for drugs and explosives, comprises a plurality of hollow interconnected sections. Their internal surfaces, including collars supporting inner tubes co-axially with outer tubes, are of inert plastics material such as PTFE and are substantially continuous through a coupling between each pair of adjacent sections. The couplings each include a pair of spring catches having teeth to be held in an annular groove by a slidable sleeve. Tongues engage in cutouts to permit transmission of torque. The end section has air openings and can have a hook to allow it to be hung over the upper edge of a vehicle side. The termination section has part of a quick release coupling and can have a bend for use in orientation and manipulation. There can be one or more intermediate sections of different length, or the end section can be inter-connected directly to the termination section.

14 Claims, 6 Drawing Sheets

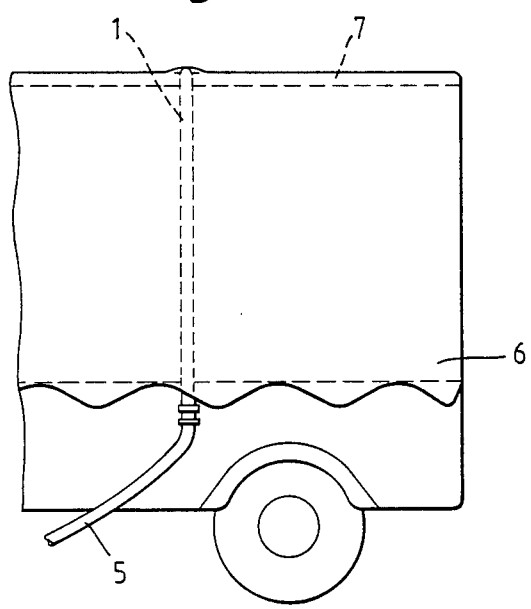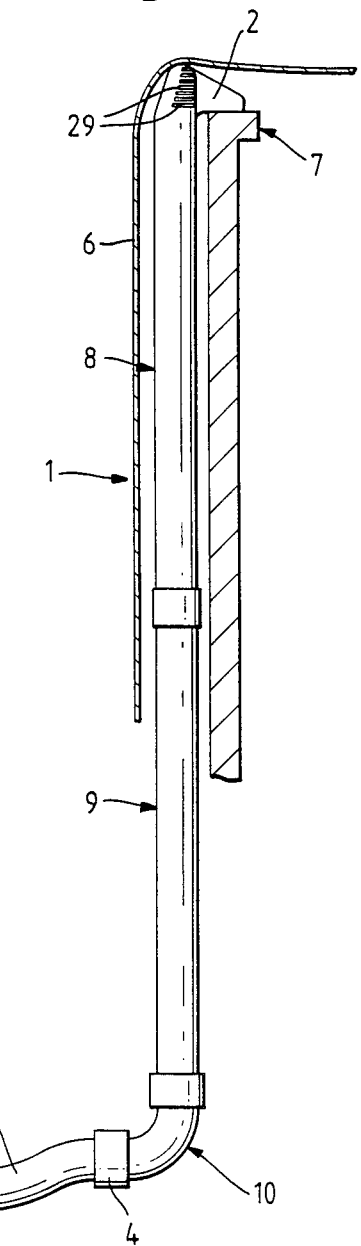

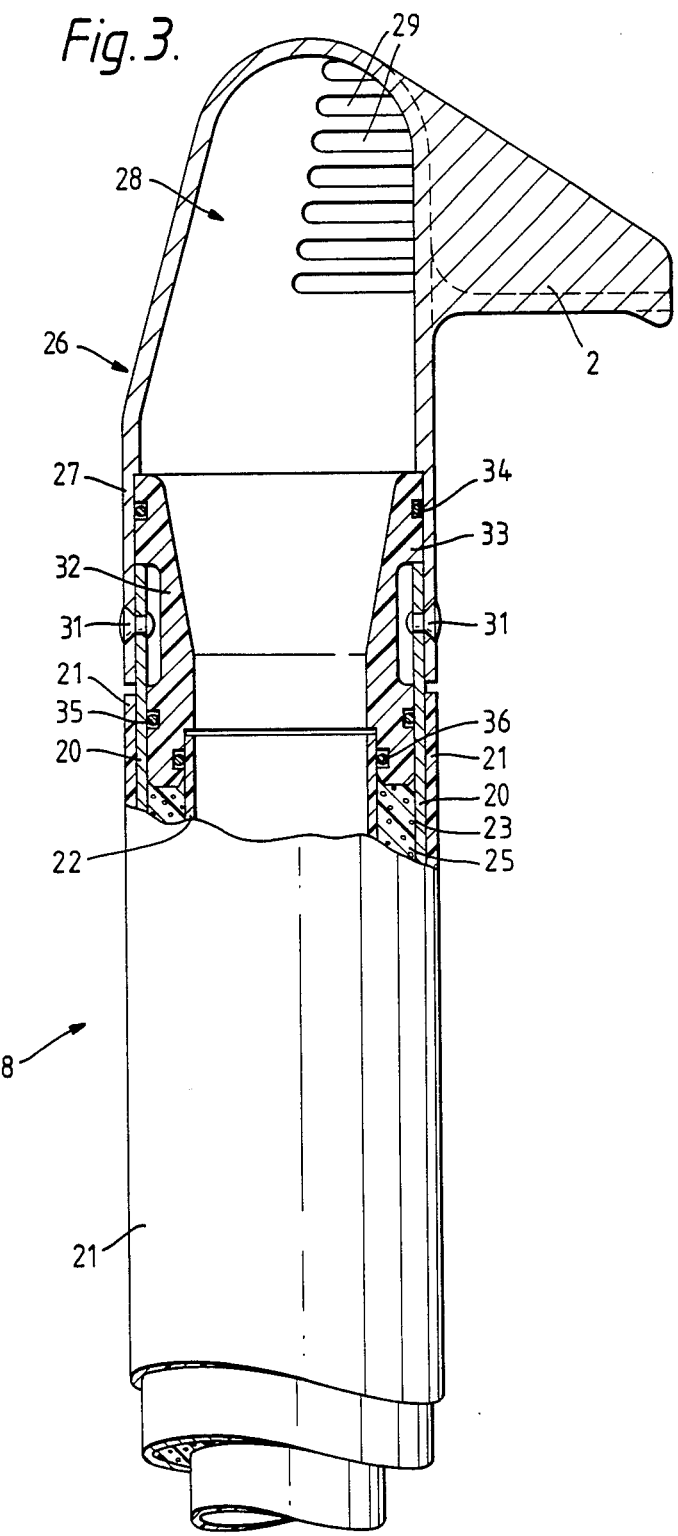

AIR WITHDRAWING SAMPLING PROBES FOR A CONTRABAND DETECTION SYSTEM

This invention relates generally to sampling probes, and relates more particularly to a sampling probe for use in conjunction with a mass analyser to sample air drawn off from within a container, typically but not exclusively a tarpaulin or canvas covered lorry, with a view to detecting certain kinds of illicit goods such as drugs and explosives carried within the container.

It is known from our U.K. patent publication GB No. 2,162,944A that cargo can be examined, at a customs entry point for example, to see if illicit goods such as drugs and explosives are being carried. Use is made of a mass analyser or 'sniffer' which is fed with air drawn from a cargo container, and which analyses that air, or more especially any dust and particulates drawn off with the air, to see if it contains traces of the illicit goods. The air sample is fed to the mass analyser through a continuous line leading from the cargo container. It is disclosed that a hole is to be bored through the cargo container to receive one end of the continuous sampling line. After the examination has been conducted, the hole is plugged to re-seal the cargo container.

An aim has been to provide a sampling probe which is more versatile.

In accordance with the present invention, a sampling probe, for use in withdrawing air from a cargo container and leading the withdrawn air towards a mass analyser, comprises a plurality of hollow inter-connected sections having internal surfaces which are of inert plastics material and are substantially continuous through a coupling between the or each adjacent pair of the inter-connected sections, one of the sections being an end section having at least one opening for allowing the air to be withdrawn into the sampling probe, and another of the sections being a termination section having a connecting member for allowing the sampling probe to be connected at least indirectly to the mass analyser.

Preferably, the or each of the couplings releasably inter-connects respective first and second adjacent sections of the sampling probe, with an end of said first section including at least one resiliently deformable projection, an end of said second section including at least one receptor, and a collar being movable relatively to said first and second sections for selectively retaining said at least one projection in said at least one receptor and thereby releasably inter-connecting said first and second sections.

More preferably, said at least one projection is in the form of two spring leaf catches, said at least one receptor is in the form of a single annular groove, and said collar is in the form of a sleeve carried by and slidable along said first of said first and second adjacent sections of the sampling probe.

The termination section may have a bend for use in orientation and manipulation of the sampling probe. The end section may have a hook for use of the sampling probe with a cargo container having an opening closed by a flexible cover. At least one intermediate section may be located between the end section and the termination section of the sampling probe.

A typical set of components may include three end sections (one with a hook, the others with different designs for taking samples through container rear doors or from vehicle cabs), three intermediate sections of different lengths), and two termination sections (either straight or with a bend), the sampling probe then including one of the end sections, one or more of the intermediate sections and one of the termination sections, although the end section could be connected directly to the termination section if appropriate in any particular application.

At least the end section, and preferably also the or each of the intermediate sections, may have an outer wall, an inner wall and spacer means for supporting the inner wall within and spaced from the outer wall to define an elongate chamber between the inner and outer walls. At least one of the elongate chambers may have heating means positioned therein for warming its inner wall, the heating means preferably being positioned in the elongate chamber of only the or each of the intermediate sections.

Further preferred features are that: the or each of the elongate chambers is filled by a foamed material; adjacent ends of the outer walls of said first and second adjacent sections are inter-lockably shaped for use in transmission of torque; the two spring leaf catches are carried by and project through apertures in the outer wall; and the internal surfaces of the sampling probe are formed of or at least coated by polytetrafluoroethylene.

Several sampling probes, in accordance with the present invention, will now be described, by way of example only, with reference to the accompanying drawings, in which:

FIG. 1 is a side view of part of a tarpaulin covered lorry indicating a potential manner of use of the present invention;

FIG. 2 is a sketch of a first sampling probe;

FIG. 3 is a partly sectioned elevation of an upper end portion of the FIG. 2 probe at its end section;

Figure 4:
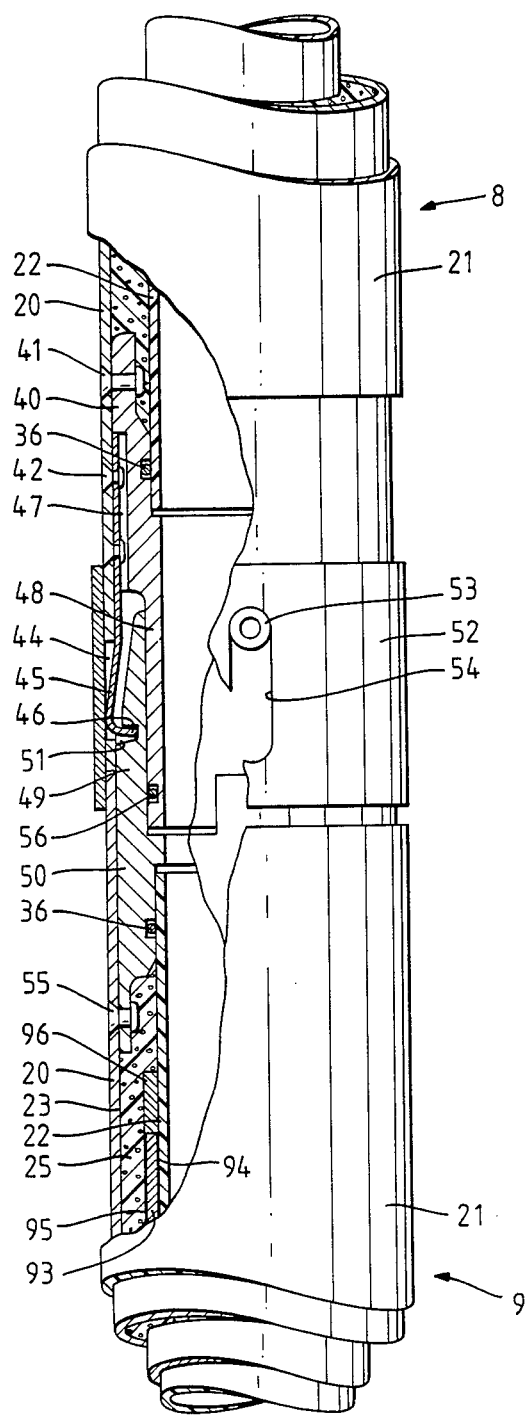
FIG. 4 is a partly sectioned elevation of a portion of the FIG. 2 probe at a position where two sections thereof are joined together.
Figure 5:
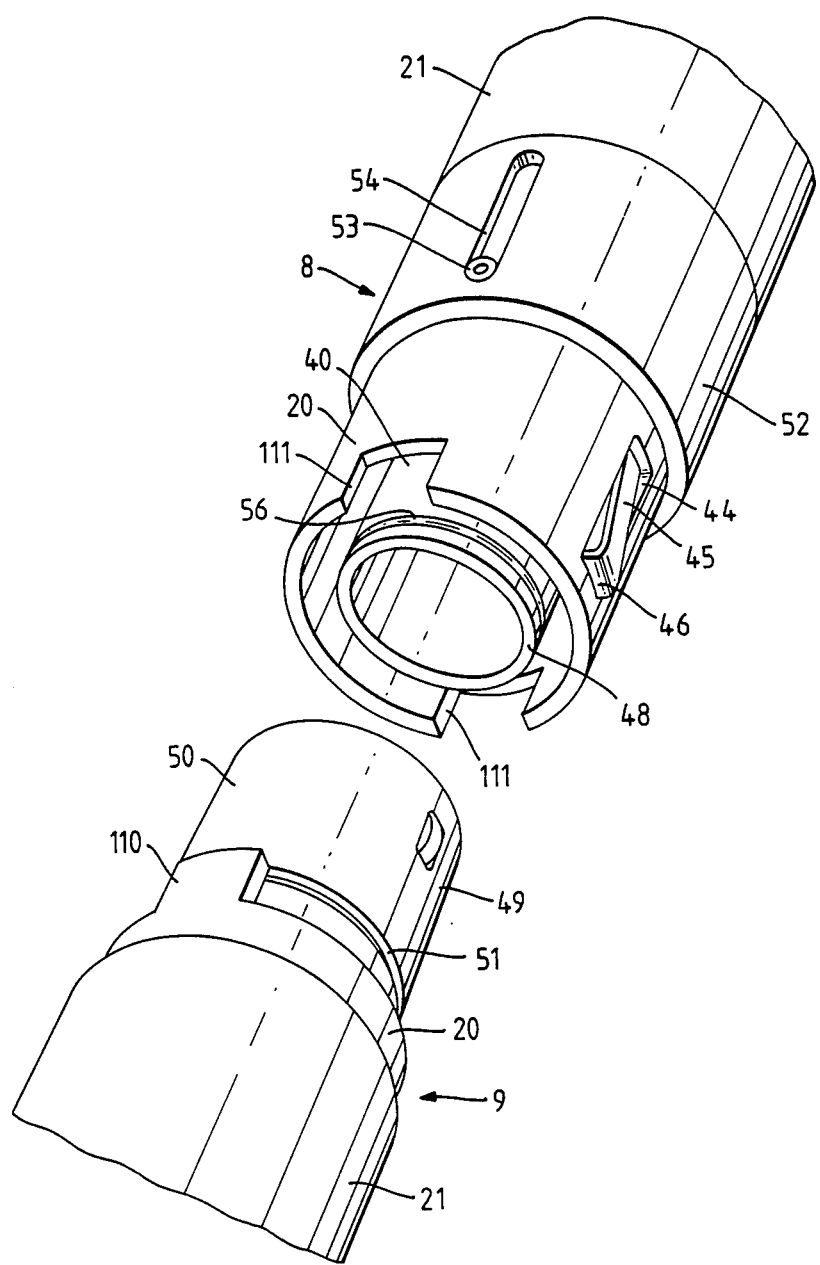
FIG. 5 is a perspective view of the portion of the FIG. 2 probe shown in FIG. 4 before its inter-connection.
Figure 6:
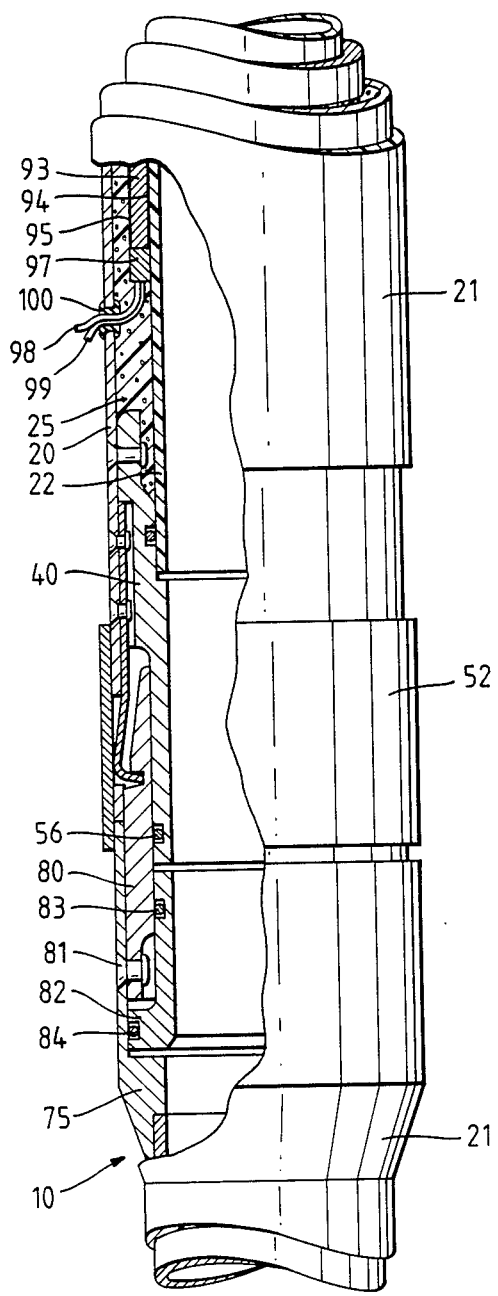
FIG. 6 is a partly sectioned elevation at the inter-connection of the FIG. 2 probe at its intermediate and termination sections.

The probes of FIGS. 2 to 7 are especially intended for use in sampling the air within a tarpaulin covered lorry as shown in FIG. 1.

Each of the probes comprises a tube 1 having a hook 2 at its upper end and a union or connecting member 4 at its other end for being connected to a flexible conduit 5 leading to a mass analyser (not shown). The connecting member 4 is the male part of a proprietary quick release coupling and can couple directly to the female part which is provided on the flexible conduit 5. Each of the probes can be inserted between a tarpaulin 6 and a side of the lorry and be hooked over an upper edge 7 of the lorry side. Often, the distance between the lower edge of the tarpaulin 6 and the ground is smaller than the distance between that lower edge and the upper edge 7 of the lorry side. To overcome this difficulty, the probes are made in several sections, for example three sections 8, 9 and 10 as in FIGS. 2 to 6, or two sections 8 and 9 as in FIG. 7. First the end or upper section 8 is pushed up inside the tarpaulin 6, then the intermediate or lower section 9 is connected to the section 8 and pushed up further until the hook 2 lies above the edge 7. The flexible conduit 5 is now connected either directly to the lower section 9, or indirectly to the intermediate section 9 through the termination section 10. Finally, each of the probes is turned so that the hook 2 lies over the edge 7. As will be appreciated, the tarpaulin 6 on a tarpaulin covered lorry is stiff, heavy and tightly tied down and the probes need to be sufficiently strong to allow a good deal of effort to be applied to raise the tarpaulin 6 clear of the upper edge 7.

With particular reference to the probe of FIGS. 2 to 6, its end section 8 comprises an outer tube 20 formed of a metal such as an aluminium alloy enclosed within a sleeve 21 formed of a heat shrinkable material which has been shrunk down onto the tube 20 to provide protection. Nested within the tube 20 is an inner thin-walled tube 22 made of polytetrafluorethylene (PTFE). The outside diameter of tube 22 is smaller than the inside diameter of tube 20 so that an annular elongate chamber 23 is formed between the two tubes, the chamber 23 being filled with foam insulating material 25.

At the upper end of the end section 8 of the probe (FIG. 3), the sleeve 21 terminates a short way down from the end of the tube 20 and there is fitted over the exposed end of the tube 20 a probe tip 26 which comprises a short tubular section 27 joined to an inclined, tapered chamber 28 having slots 29 formed therein for the entry of air. The hook 2 comprises an approximately triangular member which is secured to the tapered chamber 28, for example by welding, or is cast integrally therewith. The section 27 of the probe tip 26 is secured to the tube 20 by pop rivets 31, and inserted within the tube 20 is a PTFE collar 32 having a portion 33 which extends over the rim of the tube 20 so as to lie against the inner surface of the section 27. Sealing is provided at this point by an O ring seal 34 lying within an annular groove formed in the portion 33 of the collar 32. Moving from the interior of the probe tip 26, the internal diameter of the collar 32 is tapered down to the diameter of the inner tube 22 and then widens out again stepwise to receive the upper end of the inner tube 22 and support it co-axially within the tube 20. O ring seals 35 and 36 seal the collar 32 respectively to the tubes 20 and 22.

At the lower end of the end section 8 (FIGS. 4 and 5), the tube 22 is similarly supported by a collar 40 fixed to the tube 20 by pop rivets 41. Near its lower end, the tube 20 has two diametrically opposite slots 44. Near each slot 44, a spring leaf catch 45 is attached to the inner surface of the tube 20 by pop rivets 42, the collar 40 being formed with two diametrically opposite grooves 47 to provide room for the catches 45. The catches 45 bend outwards through the slots 44 and then turn in again to form respective catch teeth 46. The collar 40 is formed with a thin-walled narrowed-diameter end section 48 which fits within a protruding portion 49 of a collar 50 fitted within the upper end of the tube 20 of the adjacent intermediate section 9. This protruding portion 49 of the collar 50 has a tapering outer surface and an annular groove 51 formed therein. The groove 51 lies beneath the catch teeth 46 of the spring catches 45 when the two sections 8 and 9 are fully engaged.

A sliding cylindrical sleeve 52, formed of for example an aluminium alloy, fitted over the lower end of the tube 20 of the end section 8 and located by a pop rivet 53 extended through a slot 54 in the cylindrical sleeve 52, can be slid down over the spring catches 45 to push the catch teeth 46 thereof into the annular groove 51 in the protruding portion 49 of the collar 50 secured by pop rivets 55 to the tube 20 of the intermediate section 9, thereby securing the two probe sections 8 and 9 together, with sealing between the two probe sections 8 and 9 being provided by O ring seal 56.

The construction of the intermediate section 9 is generally similar to that of the major part of the end section 8, that is excluding the probe tip 26, and thus includes the above-noted tube 20 which is spaced from inner tube 22 by the above-noted collar 50. However, the chamber 23 between the tubes 20 and 22 of the intermediate section 9 has heating means in the form of a heater tape 93 laid lengthwise along the tube 22. In fact, the tube 22 is first wrapped with self-adhesive aluminium tape 94, the heater tape 93 then being laid along and over the aluminium tape 94, which conducts the heat from the heater tape 93 uniformly around the tube 22. A further layer of aluminium tape 95 is laid over the heater tape 93, which is terminated near the upper end of the intermediate section 9 by blanking piece 96. The chamber 23 is filled with a polyurethane type foam 25 which not only bonds the tube 20 to the tube 22 thereby enhancing the strength of the composite tube but also provides thermal insulation. The aluminium tape 95 protects the foam 25 from the concentrated heat from the heater tape 93.

At the lower end of the intermediate section 9 (FIG. 6), the heater tape 93 is joined by a termination connector 97 to a pair of wires 98 and 99 which are led out through a rubber grommet 100 to the outside of the shrink-wrapped sleeve 21. The lower end of the tube 22 is supported on a collar 40 which is identical to that at the lower end of the end section 8. The intermediate section 9 thus couples to the termination section 10, which includes an elbow, in a similar fashion to the coupling of the end section 8 to the intermediate section 9. However, the collar 80 is attached to elbow body 75 by pop rivets 81. Adaptor 82 provides a seal between the collar 80 and the body 75 by means of O ring seals 83 and 84. The other end of the termination section 10 (not shown), terminates in the male half 4 of a proprietary quick release coupling which mates with the female half secured to the flexible conduit 5 as already described. The shrink-wrapped sleeve 21 is carried on over and around the body 75.

Figure 7:
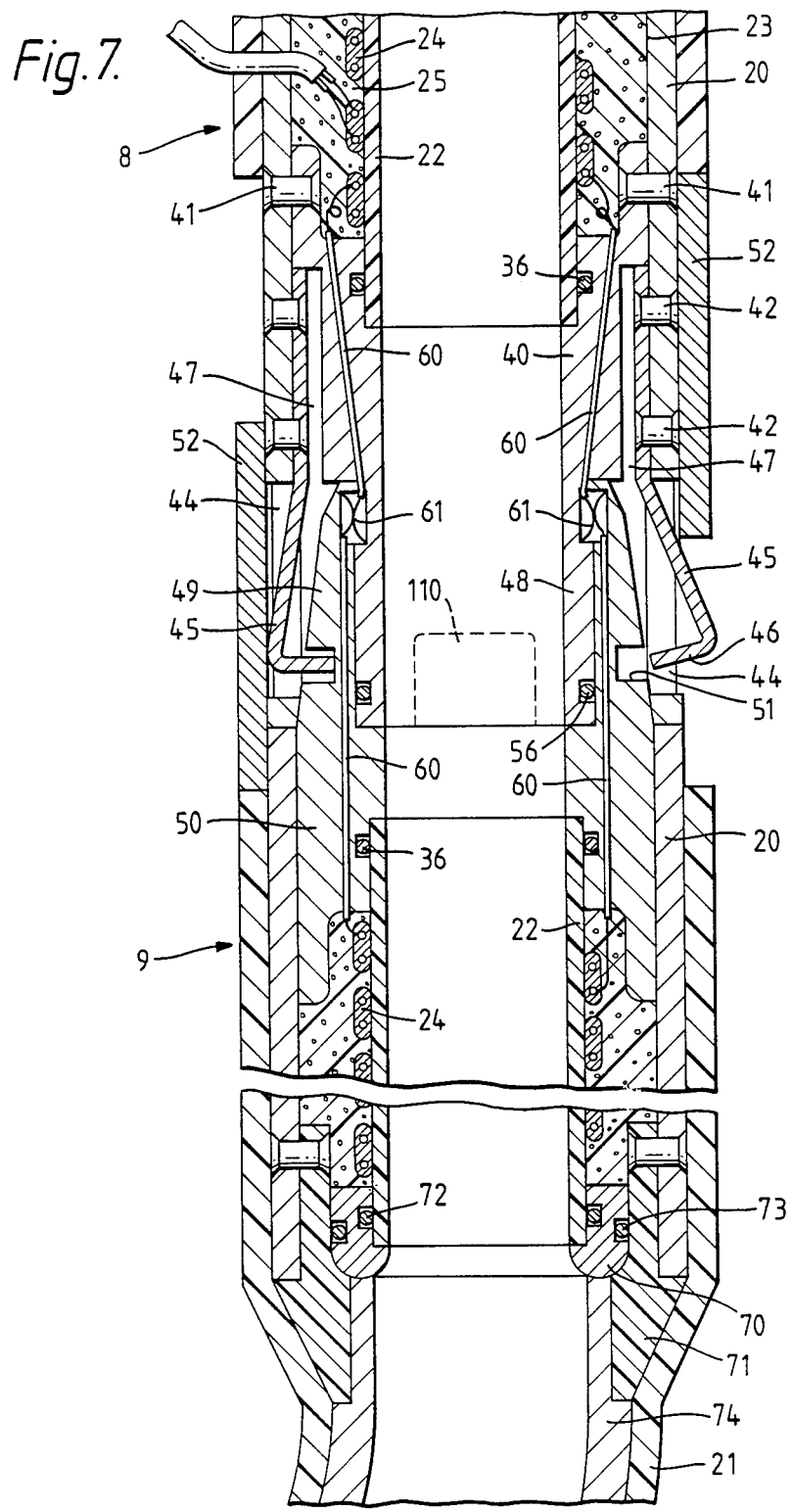
FIG. 7 is similar to FIG. 4 but of a second sampling probe.

A modified probe is shown in FIG. 7, wherein heater tape 24 extends through the inter-connection between upper (end) section 8 and lower (termination) section 9. The heater tape 24 includes two spaced conductors between which there extends resistive material so that an electrical current applied to the two conductors at one end of the tape 24 flows between the two conductors through the resistive material to produce a heating effect. Electrical through connections between the heating tapes 24 in the upper and lower probe sections 8 and 9 are made by way of wires 60 extending through bores formed in the two collars 40 and 50, and connected to respective spring contacts 61 fitted in suitable spaces formed in the exterior surface of portion 48 of the collar 40 and the interior surface of portion 49 of the collar 50. The sleeve 52 is shown as operative on the left and inoperative on the right. At the lower end of the lower section 9, the inner tube 22 is supported within a ring seal member 70 which in turn is supported by a plastics spacer 71, sealing being provided by O rings 72 and 73 fitted in grooves in the inner and outer surfaces of the ring seal member 70. The spacer 71 fits over one end of an elbow conduit 74 which, at its other end (not shown) terminates in the connecting member 4.

As may be seen, the various collars merge with the inner tubes 22 in each section so that their internal surfaces are continuous through the inter-connections between the various probe sections. Further, the inner tubes 22 are properly co-axially supported in the outer tubes 20 by being supported at each end by the various collars.

Instead of the sliding sleeve 52 for squeezing the spring catches 45 together, a rotatable cylindrical member (not shown) with two slots therein could be provided, the member being rotatable to bring its slots into alignment with the spring catches and hence allow them to spring outwards and release the sections from one another, or being rotatable to cover the springs and push them inwards.

The upper end of the lower tube 20 at each inter-connection, and the upper end of the body 75, is provided with two upwardly extending tongues 110 which engage, when the adjacent pair of sections are interconnected, with corresponding cutouts 111 formed in the lower end of the upper tube 20, thereby permitting a turning movement applied to the elbow to be transmitted to the lower and upper probe sections, necessary if the probe is to be hooked over the side wall of a lorry.

The heating arrangements may be varied. For example, it may be possible to carry the electrical supply through the spring catches 45 provided that suitable insulation is provided or there could simply be a fly lead provided on one section which, in use, is plugged into a suitable connector provided on the other section. Further, it may be necessary to heat the whole of the probe, or at least the end and intermediate sections of the probe.

The various O ring seals used in the illustrated probe can be made of Viton (TM). Instead of PTFE, the inner tubes and collars can be either made of or at least coated by another suitable inert plastics material—appropriate materials will be known to those skilled in the art. Coating by PTFE, both inside and out, is possible by means of spray coating.

I claim:

1. A sampling probe, for use in a contraband detection system for withdrawing air from a cargo container and leading the withdrawn air towards a mass analyzer, comprising a plurality of hollow inter-connected sections having internal surfaces which are of inert plastics material and are substantially continuous through at least one coupling between at least one adjacent pair of the inter-connected sections, one of the sections being an end section having at least one opening for allowing the air to be withdrawn into the sampling probe, and another of the sections being a termination section having a connecting means for allowing the sampling probe to be connected at least indirectly to the mass analyzer, wherein the end section comprises means for insertion between a non-rigid cargo covering and cargo to permit sampling of air from above the cargo and below the non-rigid cargo covering and wherein the end section includes a protrusion means configured so that, after the sampling probe is slid between the non-rigid cargo covering and the cargo, the sampling probe is rotatable so that the protrusion means acts to retain the sampling probe in position.

2. A sampling probe according to claim 1, in which each of said at least one coupling releasably interconnects respective first and second adjacent sections of the sampling probe, with an end of said first section including at least one resiliently deformable projection, an end of said second section including at least one receptor, and a collar being movable relatively to said first and second sections for selectively retaining said at least one projection in said at least one receptor and releasably inter-connecting said first and second sections.

3. A sampling probe according to claim 2, in which said at least one projection is in the form of two spring leaf catches, said at least one receptor is in the form of a single annular groove, and said collar is in the form of a sleeve carried by and slidable along said first of said first and second adjacent sections of the sampling probe.

4. A sampling probe according to claim 1, in which the termination section has a bend comprising means for orientation and manipulation of the sampling probe.

5. A sampling probe according to claim 1, in which the end section has a hook means for use of the sampling probe with a cargo container having an opening closed by a flexible cover.

6. A sampling probe according to claim 1, in which at least one intermediate section is located between the end section and the termination section of the sampling probe.

7. A sampling probe according to claim 1, in which at least the end section has an outer wall, an inner wall and spacer means for supporting the inner wall within and spaced from the outer wall to define an elongate chamber between the inner and outer walls.

8. A sampling probe according to claim 7, in which at least one intermediate section is located between the end section and the termination section of the sampling probe, and each of said at least one intermediate section also has a respective outer wall, inner wall and spacer means defining an elongate chamber.

9. A sampling probe according to claim 7, in which at least one of the elongate chambers has heating means positioned therein for warming its inner wall.

10. A sampling probe according to claim 9, in which at least one intermediate section is located between the end section and the termination section of the sampling probe, each of said at least one intermediate section also has a respective outer wall, inner wall and spacer means defining an elongate chamber, and the heating means is positioned in the elongate chamber of only each of said at least one intermediate section.

11. A sampling probe according to claim 7, in which each of the at least one elongate chambers is filled by a foamed material.

12. A sampling probe according to claim 7, in which each of said at least one coupling releasably interconnects respective first and second adjacent sections of the sampling probe, with an end of said first section including at least one resiliently deformable projection, an end of said second section including at least one receptor, and a collar being movable relatively to said first and second sections for selectively retaining said at least one projection in said at least one receptor and releasably inter-connecting said first and second sections, and adjacent ends of the outer walls of said first and second adjacent sections are inter-lockably shaped for use in transmission of torque.

13. A sampling probe according to claim 12, in which said at least one projection is in the form of two spring leaf catches which are carried by and project through apertures in the outer wall.

14. A sampling probe according to claim 1, in which the internal surfaces of the sampling probe are of polytetrafluoroethylene.

* * * * *